United States Patent
Milanov et al.

(10) Patent No.: US 10,780,422 B2
(45) Date of Patent: Sep. 22, 2020

(54) RHENIUM-DOPED CATALYST AND A METHOD FOR THE SELECTIVE METHANATION OF CARBON MONOXIDE

(71) Applicant: BASF SE, Ludwigshafen (DE)

(72) Inventors: Andrian Milanov, Mannheim (DE); Ekkehard Schwab, Neustadt (DE); Mike Hoffmann, Kaiserslautern (DE); Stefan Kotrel, Weinheim (DE); Stefan Altwasser, Stuttgart (DE)

(73) Assignee: BASF SE (DE)

( * ) Notice: Subject to any disclaimer, the term of this patent is extended or adjusted under 35 U.S.C. 154(b) by 0 days.

(21) Appl. No.: 15/561,737

(22) PCT Filed: Mar. 23, 2016

(86) PCT No.: PCT/EP2016/056418
§ 371 (c)(1),
(2) Date: Sep. 26, 2017

(87) PCT Pub. No.: WO2016/151031
PCT Pub. Date: Sep. 29, 2016

(65) Prior Publication Data
US 2018/0085739 A1 Mar. 29, 2018

(30) Foreign Application Priority Data
Mar. 26, 2015 (EP) .................... 15161099

(51) Int. Cl.
| | |
|---|---|
| *B01J 23/46* | (2006.01) |
| *B01J 23/656* | (2006.01) |
| *B01J 23/75* | (2006.01) |
| *B01J 23/755* | (2006.01) |
| *B01J 23/889* | (2006.01) |
| *C07C 1/04* | (2006.01) |
| *B01J 23/10* | (2006.01) |
| *B01J 21/06* | (2006.01) |
| *B01J 37/02* | (2006.01) |
| *B01J 35/00* | (2006.01) |
| *C10K 3/04* | (2006.01) |
| *B01J 35/10* | (2006.01) |
| *C10L 3/08* | (2006.01) |
| *C01B 3/58* | (2006.01) |
| *B01J 23/36* | (2006.01) |
| *B01J 37/00* | (2006.01) |

(52) U.S. Cl.
CPC ........... *B01J 23/462* (2013.01); *B01J 21/066* (2013.01); *B01J 23/10* (2013.01); *B01J 23/36* (2013.01); *B01J 23/464* (2013.01); *B01J 23/6567* (2013.01); *B01J 23/75* (2013.01); *B01J 23/755* (2013.01); *B01J 23/8896* (2013.01); *B01J 35/002* (2013.01); *B01J 35/1014* (2013.01); *B01J 37/0009* (2013.01); *B01J 37/0201* (2013.01); *C01B 3/586* (2013.01); *C07C 1/04* (2013.01); *C07C 1/0435* (2013.01); *C10K 3/04* (2013.01); *C10L 3/08* (2013.01); *B01J 37/0205* (2013.01); *B01J 2523/00* (2013.01); *B01J 2523/3706* (2013.01); *B01J 2523/3712* (2013.01); *C07C 2523/10* (2013.01); *C07C 2523/36* (2013.01); *C07C 2523/46* (2013.01)

(58) Field of Classification Search
None
See application file for complete search history.

(56) References Cited

U.S. PATENT DOCUMENTS

| | | | |
|---|---|---|---|
| 3,615,164 A | 10/1971 | Baker et al. | |
| 3,663,162 A | 5/1972 | Randhava | |
| 4,567,205 A | 1/1986 | Arcuri et al. | |
| 7,560,496 B2 | 7/2009 | Kuhrs et al. | |
| 8,093,178 B2 | 1/2012 | Iwasa et al. | |
| 2005/0096211 A1 | 5/2005 | Takeda et al. | |
| 2006/0241325 A1* | 10/2006 | Komplin | B01J 23/8933 568/846 |
| 2007/0259975 A1 | 11/2007 | Lee et al. | |
| 2008/0229731 A1 | 9/2008 | Kikuhara et al. | |
| 2010/0093525 A1* | 4/2010 | Steiner | B01J 23/63 502/303 |

(Continued)

FOREIGN PATENT DOCUMENTS

| | | |
|---|---|---|
| CN | 102151570 A | 8/2011 |
| EP | 0231401 A1 | 8/1987 |

(Continued)

OTHER PUBLICATIONS

Baranowska, K. et al. "Effect of Rhenium on Ruthenium Dispersion in the Ru—Re/ γ -Al2O3 Catalysts" Catal Lett (2014) 144:447-459 (Year: 2014).*

(Continued)

*Primary Examiner* — Medhanit W Bahta
(74) *Attorney, Agent, or Firm* — Faegre Drinker Biddle & Reath LLP

(57) ABSTRACT

The present invention relates to a catalytically active composition for the selective methanation of carbon monoxide in reformate streams comprising hydrogen and carbon dioxide, comprising at least one element selected from the group consisting of ruthenium, rhodium, nickel and cobalt as active component and rhenium as dopant on a support material. The catalyst according to the invention is preferably used for carrying out methanation reactions in a temperature range from 100 to 300° C. for use in the production of hydrogen for fuel cell applications.

15 Claims, 1 Drawing Sheet

(56) References Cited

U.S. PATENT DOCUMENTS

2010/0168257 A1* 7/2010 Duisberg ............... B01J 23/889
                                                        518/715

FOREIGN PATENT DOCUMENTS

| EP | 1174486 A1 | 1/2002 |
| EP | 1246286 A1 | 10/2002 |
| EP | 1707261 A1 | 10/2006 |
| EP | 2125201 B1 | 4/2011 |
| JP | 2002068707 A | 3/2002 |
| JP | 2007-252988 A | 10/2007 |
| JP | 2008-155147 A | 7/2008 |
| JP | 2010-520807 A | 6/2010 |
| WO | WO-9743207 A1 | 11/1997 |
| WO | WO-9813294 A1 | 4/1998 |
| WO | WO-2008/075761 A1 | 6/2008 |
| WO | WO-2008101875 A1 | 8/2008 |

OTHER PUBLICATIONS

Mori, T. et al. "Promoting Effect of V, Mo, W, and Re on the Rate of G O Bond Dissociation of Adsorbed CO in Methanation on Ru/Al2O3" J. Chem. Soc., Chem. Commun., 1984, 678-679 (Year: 1984).*

International Search Report for PCT/EP2016/056418 dated Jun. 2, 2016.

Written Opinion of the International Searching Authority for PCT/EP2016/056418 dated Jun. 2, 2016.

Extended European Search Report for EP Patent Application No. 15161099.5, dated Oct. 8, 2015, 5 pages.

* cited by examiner

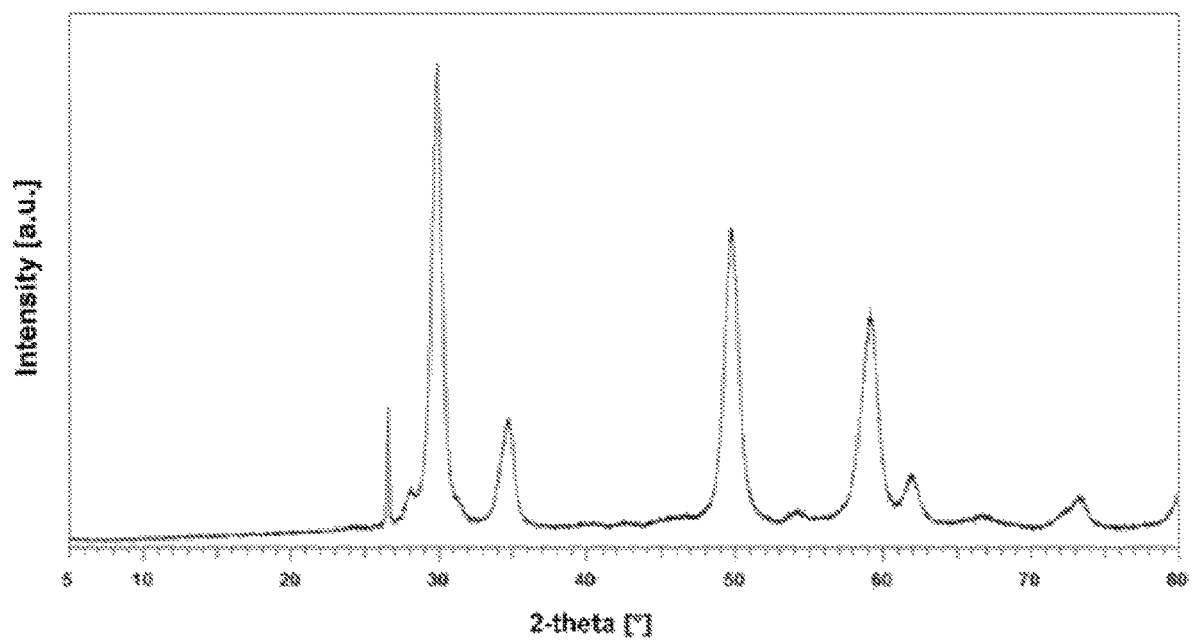

RHENIUM-DOPED CATALYST AND A METHOD FOR THE SELECTIVE METHANATION OF CARBON MONOXIDE

CROSS-REFERENCE TO RELATED APPLICATIONS

This application is a national stage application (under 35 U.S.C. § 371) of PCT/EP2016/056418, filed Mar. 23, 2016, which claims benefit of European Application No. 15161099.5, filed Mar. 26, 2015, both of which are incorporated herein by reference in their entirety.

The invention relates to a catalytic composition and a process for the selective methanation of carbon monoxide in streams comprising hydrogen and carbon dioxide, in particular for use in fuel cell systems.

Low-temperature PEM fuel cells (PEM=polymer electrolyte membrane) can be operated only using hydrogen or hydrogen-rich gases having a defined quality. In particular, the carbon monoxide (CO) concentration is a critical parameter. It depends on the energy carrier used and on the reforming process employed. Higher CO concentrations can be removed by means of the water gas shift reaction with further formation of hydrogen.

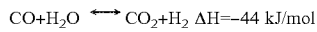

$$CO + H_2O \rightleftharpoons CO_2 + H_2 \quad \Delta H = -44 \text{ kJ/mol}$$

Since this is an equilibrium reaction, a residual concentration of CO, generally in the range from 0.25 to 1.5% by volume, remains in the gas stream as a function of process design and temperature. When catalysts having a high copper content are used, removal of CO down to 2500 ppm can, for example, be achieved. However, the CO content in the hydrogen-rich gas has to be reduced still further in order to avoid poisoning of the anode catalyst; guideline values are here a maximum of from 10 to 50 ppm.

The removal of the CO comprised from the gas stream down to the required limit values is usually carried out in a fine purification stage. Here, selective oxidation is the customary CO removal method today. The selective oxidation has been highly developed but has the disadvantages of only a moderate selectivity and the necessity of precisely metered introduction of air, which results in a high outlay for instrumentation. If the necessary ratio of oxygen to CO is not adhered to accurately, this can lead to high losses of hydrogen. Furthermore, the narrow temperature window of generally not more than 20° C. requires complicated thermal management of the reactor. In addition, there is a safety problem due to addition of the oxidant oxygen to the gas. Compared to selective CO oxidation, the removal of the CO by reaction with $H_2$ (selective methanation of CO in the presence of $CO_2$) has considerably advantages due to its undemanding implementation in process engineering terms.

The methanation of CO (hydrogenation of carbon monoxide to methane) occurs according to the reaction equation:

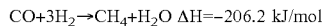

$$CO + 3H_2 \rightarrow CH_4 + H_2O \quad \Delta H = -206.2 \text{ kJ/mol}$$

As competing reaction, the conversion of $CO_2$ into methane proceeds:

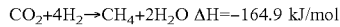

$$CO_2 + 4H_2 \rightarrow CH_4 + 2H_2O \quad \Delta H = -164.9 \text{ kJ/mol}$$

The particular challenge for selective CO methanation is that CO should be preferentially hydrogenated rather than $CO_2$, since the latter would consume further hydrogen. The CO concentration in the reformate is from about 2500 ppm to 15 000 ppm, while the $CO_2$ content at from about 15 to 25% by volume is an order of magnitude above the CO content. Accordingly, a CO-selective catalyst is indispensable for realization of the low CO concentrations demanded for, for example, PEM fuel cells.

The selective methanation of CO has been known for a long time. CO was firstly methanated over a nickel catalyst, but $CO_2$ had to be scrubbed out beforehand. In 1968, a ruthenium catalyst for selective CO methanation was claimed by Baker et al. (U.S. Pat. No. 3,615,164), with a ruthenium or rhodium catalyst on an aluminum oxide support material being used there. Likewise, the selective methanation of CO in a gas mixture comprising hydrogen, carbon dioxide and carbon monoxide at temperatures in the range from 125 to 300° C. using ruthenium-comprising catalysts has been described in Chemical Abstracts, volume 74, 1971, No. 35106u. A Raney nickel catalyst is claimed for this reaction in U.S. Pat. No. 3,663,162 of 1972.

In EP-A-1174486, a methanation stage is combined with a unit for selective oxidation with the aim of a lower oxygen consumption and a lower degree of $CO_2$ methanation. The catalyst used for the methanation comprises Ru, Pt, Rh, Pd or Ni on an aluminum oxide support.

In WO 98/13294, two methanation stages at different temperature levels are connected. The advantage here is said to be that no or less $CO_2$ is methanated at the high-temperature stage, but a large part of the carbon monoxide is removed. In the subsequent low-temperature methanation, the residual removal of CO occurs. A noble metal catalyst, in particular Ru, on an aluminum support is used.

WO 97/43207 describes the combination of a first stage for selective oxidation with a subsequent methanation stage using rhodium as active component. Using this combination, both processes are said to be able to be operated under optimal conditions.

Further, more recent applications, for example EP-A-1246286 in which a methanation reactor of a unit for selective oxidation is installed downstream as last process stage of a gas purification for the purpose of a simpler structure and better handling, use conventional catalysts, predominantly based on ruthenium or nickel.

JP-A-2002/068707 is concerned with methanation catalysts which have been applied to a refractory inorganic oxide selected from among oxides of aluminum, titanium, silicon or zirconium.

EP-A-1707261 describes a process for the selective oxidation of CO using a catalyst comprising ruthenium on a support composed of mixed metal oxides, doped with lanthanides.

U.S. Pat. No. 7,560,496 describes a process for the selective methanation of CO in the presence of $CO_2$ using a catalyst comprising ruthenium, rhodium, nickel and/or cobalt as active component and at least one further dopant selected from the group consisting of iron, niobium, manganese, molybdenum and zirconium on a support material based on carbon.

WO 2008/101875 relates to a catalytically active composition for the selective methanation of carbon monoxide in streams comprising hydrogen and carbon dioxide, which is characterized in that it comprises ruthenium as active component and a lanthanum-cerium-zirconium oxide as support material.

US-A-2005/0096211 describes the selective methanation over a catalyst composed of Ru, Rh, Ni or combinations on β-zeolite, mordenite and faujasite. Although the desired CO concentrations below 100 ppm are achieved in this way, the selectivity decreases at temperatures above 190° C., at which the catalyst displays its activity, to significantly below 50%. Since the hydrogenation of $CO_2$ removes 3/2 times as much hydrogen per mole as the hydrogenated of CO, the demand for a very high selectivity is very important. In addition, a reasonable catalytic activity is achieved only over the very small temperature window from 170° C. to 180° C.

The processes of the prior art do not make it possible to achieve satisfactory lowering of the CO content while sparing the $CO_2$ content. The catalysts developed hitherto either do not work selectively enough or are effective only in a very narrow temperature range. The very narrow temperature range in particular makes industrial implementation of the "selective methanation" concept very difficult. This is because as soon as the selectivity drops, heating of the reactor occurs, which leads to further methanation of $CO_2$ and thus to thermal "runaway" of the process unit. The exothermic nature of the reaction thus results in hot spots. For this reason, it has to be possible to operate in a broad temperature window. A further problem is the adiabatic temperature increase in monoliths when these are used as shaped catalyst bodies, which is often the case in practice.

For fuel cell applications in particular, the demanded maximum CO content in the hydrogen-rich gas fed in and the required high selectivity (methanation of CO but not of $CO_2$) over a broad temperature window still represents a large development potential for suitable deactivation-resistant catalysts.

It was therefore an object of the invention to provide a catalyst for selective CO methanation which maintains its selectivity and activity in a broad temperature range.

The object has been achieved according to the invention by using a catalytically active composition comprising ruthenium, rhodium, nickel or cobalt or mixtures thereof as active component and rhenium as doping element on a suitable support material for the selective methanation of carbon monoxide in reformate streams comprising hydrogen and carbon dioxide.

It has surprisingly been found that a catalyst comprising ruthenium, rhodium, nickel or cobalt or mixtures thereof as active component and rhenium as doping element on a suitable support material is able to ensure the methanation of CO in a wide temperature range from about 100 to 300° C. at a virtually constant selectivity over a long period of time. Conventional catalysts display a significant decrease in selectivity with increasing temperature and prolonged times on stream. Use of the catalyst according to the invention requires a significantly smaller outlay for regulation since the temperature window in the methanation of CO has to be adhered to less precisely. In addition, a catalyst which also works well at high temperatures can be installed directly downstream of the purification stage (TTC—low temperature conversion) which is operated at from about 220 to 280° C.

The invention accordingly provides a catalytically active composition for the selective methanation of carbon monoxide in reformate streams comprising hydrogen and carbon dioxide, comprising at least one element selected from the group consisting of ruthenium, rhodium, nickel and cobalt as active component and rhenium as dopant on a support material.

Embodiments of the present invention can be derived from the claims, the description and the examples. It goes without saying that the features mentioned above and the features still to be explained below of the subject matter of the invention can be used not only in the combinations indicated in each case but also in other combinations without going outside the scope of the invention.

The catalytically active composition comprises at least one element selected from the group consisting of ruthenium, rhodium, nickel and cobalt, preferably ruthenium, as active component. The active component is preferably present as oxide in the catalyst. The actual active composition is then produced in situ by activation with hydrogen.

An ex-situ prereduction with, for example, hydrogen, a hydrogen-nitrogen mixture or another suitable reducing agent is likewise possible. In this case, the active component of the catalyst is present in metallic form. The catalyst can be installed in the reactor either in this form or else after subsequent surface passivation of the metallic component.

Suitable support materials are, according to the invention, all materials which are usually able to be used in catalyst chemistry for these purposes and have a sufficiently high BET surface area and an appropriate porosity (pore volume). Mention may be made by way of example of support materials selected from the group consisting of $Al_2O_3$, $ZrO_2$, $TiO_2$, SIC, ZnO, oxides of the Group IIA metals, oxides of transition metals of Groups IIIB, IVB, VB, VIB, oxides of metals of the rare earths, aluminosilicates, zeolites, MOFs (metal organic frameworks) and mixtures thereof.

Supports which are preferably used according to the invention are materials of this type selected from the group consisting of $Al_2O_3$, $ZrO_2$, $TiO_2$ and oxides of metals of the rare earths.

One support material which is particularly preferred according to the invention is a lanthanum-cerium-zirconium oxide (LaCeZr oxide) having a lanthanum oxide content of from 0.1 to 15% by weight, preferably from 1 to 10% by weight and particularly preferably from 3 to 7% by weight. The cerium oxide content is from 0.1 to 20% by weight, preferably from 1 to 17% by weight and particularly preferably from 10 to 16% by weight, in each case based on the weight of the total support material.

The zirconium oxide content of the support material is advantageously from 30 to 99.8% by weight. In preferred embodiments, it is a content which together with the proportions by weight of lanthanum oxide and cerium oxide and optionally further constituents as described below adds up in each case to 100% by weight.

In a preferred embodiment, the support used according to the invention is a support whose physicochemical properties such as BET surface area, pore volume and lateral compressive strength have preferred values.

The BET surface area of the support materials used for the catalysts of the invention is at least 10 $m^2/g$, advantageously at least 20 $m^2/g$, preferably at least 40 $m^2/g$, particularly preferably at least 60 $m^2/g$ and very particularly preferably at least 80 $m^2/g$. The BET surface area is determined by a method in accordance with DIN 66131.

The pore volume of the support material is advantageously in the range from 0.05 to 1.5 $cm^3/g$, preferably in the range from 0.1 to 1.0 $cm^3/g$, particularly preferably in the range from 0.15 to 0.9 $cm^3/g$, very particularly preferably in the range from 0.17 to 0.7 $cm^3/g$, in particular in the range from 0.2 to 0.6 $cm^3/g$. The pore volume is determined by the method of mercury porosimetry in accordance with DIN 66133.

In the case of support materials in the form of shaped bodies (e.g. pellets, extrudates, spherical particles, etc), their compressive strength is advantageously at least 0.2 kgf, preferably at least 0.5 kgf, particularly preferably at least 1.0 kgf, very particularly preferably at least 1.5 kgf, in particular at least 2.0 kgf. The lateral compressive strength is a measure of the stability of a material when pressure is exerted on its side faces. The material is for this purpose clamped between two punches (initial force 0.5 N) which then move toward one another at a test speed of 1.6 mm/min and crush the material. The force required for crushing the material is recorded. Data are derived from a statistical evaluation of at least 20 shaped bodies.

The support material used according to the invention can comprise not only the abovementioned components but also further materials which can be customarily used for these purposes in catalyst chemistry, for example aluminum oxide. Binder materials which have a sufficiently high BET surface area are also suitable. The BET surface area of these binder materials which are additionally used should advantageously be at least 120 m$^2$/g.

The content of these binder materials should not exceed 70% by weight, preferably 50% by weight, particularly preferably 30% by weight and very particularly preferably 20% by weight, in each case based on the weight of the total support material.

The loading of the support material with at least one of the abovementioned active components according to the invention is from 0.1 to 20% by weight, preferably from 0.2 to 10% by weight, particularly preferably from 0.3 to 5% by weight, very particularly preferably from 0.4 to 4.5% by weight, in particular from 0.5 to 3% by weight. Further advantageous ranges of the amount are, for example, from 0.1 to 10% by weight, from 0.5 to 5% by weight and also from 0.7 to 4 and from 1 to 3% by weight. The figures are in each case based on the total weight of the catalytically active composition.

The loading of the support material with rhenium as doping element is from 0.01 to 20% by weight, preferably from 0.05 to 10% by weight, particularly preferably from 0.07 to 5% by weight, very particularly preferably from 0.08 to 4% by weight, in particular from 0.1 to 3% by weight. The figures are in each case based on the total weight of the catalytically active composition.

A preferred composition of the catalytically active system of the invention comprises from 0.01 to 20% by weight, preferably from 0.07 to 5% by weight, particularly preferably from 0.08 to 4% by weight, of rhenium and from 0.1 to 20% by weight, preferably from 0.5 to 5% by weight, particularly preferably from 1 to 3% by weight, of ruthenium, based on the total weight of the catalytically active composition, on a support selected from the group consisting of Al$_2$O$_3$, ZrO$_2$, TiO$_2$ and metal oxides of the rare earths, preferably on a support composed of ZrO$_2$.

A further preferred composition of the catalytically active system of the invention comprises from 0.01 to 20% by weight, preferably from 0.07 to 5% by weight, particularly preferably from 0.08 to 4% by weight, of rhenium and from 0.1 to 20% by weight, preferably from 0.2 to 10% by weight, particularly preferably from 0.3 to 5% by weight, of ruthenium, based on the total weight of the catalytically active composition, on a support selected from the group consisting of zeolite A, β-zeolite, mordenite, faujasite, ZSM-5 and MOF.

A further preferred composition of the catalytically active system comprises from 0.01 to 20% by weight of rhenium and from 0.1 to 20% by weight of ruthenium, based on the total weight of the catalytically active composition, on a lanthanum-cerium-zirconium oxide support having a lanthanum oxide content of from 0.1 to 15% by weight and a cerium oxide content of from 0.1 to 20% by weight, in each case based on the weight of the total support material.

A further preferred composition of the catalytically active system comprises from 0.05 to 10% by weight of rhenium and from 0.5 to 5% by weight of ruthenium, based on the total weight of the catalytically active composition, on a lanthanum-cerium-zirconium oxide support having a lanthanum oxide content of from 0.1 to 15% by weight and a cerium oxide content of from 0.1 to 20% by weight, in each case based on the weight of the total support material.

A further preferred composition of the catalytically active system comprises from 0.07 to 5% by weight of rhenium and from 0.7 to 4% by weight of ruthenium, based on the total weight of the catalytically active composition, on a lanthanum-cerium-zirconium oxide support having a lanthanum oxide content of from 0.1 to 10% by weight and a cerium oxide content of from 0.1 to 17% by weight, in each case based on the weight of the total support material.

A particularly preferred composition of the catalytically active system comprises from 0.08 to 4% by weight of rhenium and from 1 to 3% by weight of ruthenium, based on the total weight of the catalytically active composition, on a lanthanum-cerium-zirconium oxide support having a lanthanum oxide content of from 3 to 7% by weight and a cerium oxide content of from 10 to 16% by weight, in each case based on the weight of the total support material.

In a preferred embodiment, the catalyst of the invention has preferred values of its physicochemical properties such as phase composition determined by XRD, BET surface area, pore volume and lateral compressive strength.

Thus, in a preferred embodiment of the catalyst of the invention, the XRD pattern recorded in the 2θ (2 theta) range from 5° to 80° displays at least the reflections at 26.54° 2θ (2 theta), 28.12° 2θ (2 theta), 29.90° 2θ (2 theta), 34.55° 2θ (2 theta), 49.70° 2θ (2 theta), 53.90° 2θ(2 theta), 59.12° 2θ (2 theta), 61.96° 2θ (2 theta), 66.42° 2θ (2 theta), 73.48° 2θ (2 theta).

The XRD analyses were carried out using a D8 Advance series 2 from Bruker/AXS using a CuK-alpha source (having a wavelength of 0.154 nm at 40 kV and 40 mA) and θ-θ geometry (Bragg-Brentano geometry) in the reflection mode. The measurements were carried out over the measurement range: 5-80° (2 theta), 0.02° steps with 3.6 seconds/step.

In a further preferred embodiment, the BET surface area of the catalyst of the invention is at least 10 m$^2$/g, advantageously at least 20 m$^2$/g, preferably at least 40 m$^2$/g, particularly preferably at least 60 m$^2$/g and very particularly preferably at least 80 m$^2$/g. The BET surface area was determined in accordance with DIN 66131.

In a further preferred embodiment, the pore volume of the catalyst of the invention is advantageously in the range from 0.05 to 1.5 cm$^3$/g, preferably in the range from 0.1 to 1.0 cm$^3$/g, particularly preferably in the range from 0.15 to 0.9 cm$^3$/g, very particularly preferably in the range from 0.17 to 0.7 cm$^3$/g, in particular in the range from 0.2 to 0.6 cm$^3$/g. The method of mercury porosimetry in accordance with DIN standard 66133 was employed for determining the pore volume.

In a preferred embodiment, the catalyst of the invention is present as shaped bodies (e.g. pellets, extrudates, spherical particles, etc), with the compressive strength of the shaped bodies advantageously being at least 0.2 kgf, preferably at least 0.5 kgf, particularly preferably at least 1.0 kgf, very particularly preferably at least 1.5 kgf, in particular at least 2.0 kgf. The lateral compressive strength is a measure of the stability of a material when pressure is exerted onto its lateral surfaces. The material is for this purpose clamped between two punches (preliminary force 0.5 N) which then move toward one another at a test speed of 1.6 mm/min and crush the material. The force required for crushing the material is recorded. Data are obtained by a statistical evaluation of at least 20 shaped bodies.

Further embodiments of the composition of the catalyst used according to the invention may be found in the examples. It goes without saying that the abovementioned features and features still to be indicated below of the catalyst can be used not only in the combinations and value ranges indicated but also in other combinations and value ranges within the restrictions of the main claim, without going outside the scope of the invention.

The catalyst used according to the invention is produced in a conventional way, for example by bringing the active component and optionally the doping element, preferably in the form of their salts/hydrates, into solution and then applying them to the support in a suitable manner, for example by impregnation. The catalyst is then dried, calcined, optionally reduced and optionally passivated.

The application of the active components to the support material by impregnation can be carried out in a conventional way, e.g. as washcoat onto a monolith. Procedure and process conditions are described, for example, in the Handbook of heterogeneous catalysis, 2nd edition, Vol. 1, VCH Verlagsgesellschaft Weinheim, 2008, pages 57 to 66 and 147 to 149.

An alternative production method comprises kneading of the support materials with the salts/hydrates of the active elements and optionally doping elements with subsequent extrusion, drying and optionally calcination, optionally reduction and optionally passivation.

Here, the kneading of the support material with the active compositions and also the further working steps can be carried out in a conventional way using known apparatuses.

The production of shaped bodies from pulverulant raw materials can be carried out by conventional methods known to those skilled in the art, for example tableting, aggregation or extrusion, as are described, inter alia, in the Handbook of Heterogeneous Catalysis, vol. 1, VCH Verlagsgesellschaft Weinheim, 1997, pages 414-417.

In the shaping or the application, auxiliaries known to those skilled in the art, e.g. binders, lubricants and/or solvents, can be added.

A catalytically active composition which is highly suitable for the selective methanation of carbon monoxide in reformate streams comprising hydrogen and carbon dioxide is formed. Depending on the respective reaction conditions, the desired significant reduction in the concentration of CO to below 10 ppm in the gas mixture is achieved with minimal loss of hydrogen.

The invention also provides for the use of a catalytically active composition for the selective methanation of carbon monoxide in reformate streams comprising hydrogen and carbon dioxide, wherein the catalytically active composition comprises at least one element selected from the group consisting of ruthenium, rhodium, nickel and cobalt, preferably ruthenium, as active component and rhenium as dopant on a support material selected from the group consisting of $Al_2O_3$, $ZrO_2$, $TiO_2$, SiC, ZnO, oxides of the Group IIA metals, oxides of the transition metals of Groups IIIB, IVB, VB, VIB, oxides of metals of the rare earths, aluminosilicates, zeolites, MOFs (metal organic frameworks) and mixtures thereof.

In a preferred embodiment of the use according to the invention of the catalytically active composition for the selective methanation of carbon monoxide in reformate streams comprising hydrogen and carbon dioxide, use is made of a catalytically active composition which comprises at least one element selected from the group consisting of ruthenium, rhodium, nickel and cobalt, preferably ruthenium, as active component and rhenium as dopant on a support material, where the total loading of the support material with the active component is from 0.1 to 20% by weight and with rhenium is from 0.01 to 20% by weight, in each case based on the total weight of the catalytically active composition, and the support material comprises one or more components selected from the group consisting of $Al_2O_3$, $ZrO_2$, $TiO_2$, SIC, ZnO, oxides of the Group IIA metals, oxides of the transition metals of Groups IIIB, IVB, VB, VIB, oxides of metals of the rare earths, aluminosilicates, zeolites, MOFs (metal organic frameworks) and mixtures thereof.

In a particularly preferred embodiment of the use according to the invention of the catalytically active composition for the selective methanation of carbon monoxide in reformate streams comprising hydrogen and carbon dioxide, use is made of a catalytically active composition which comprises at least one element selected from the group consisting of ruthenium, rhodium, nickel and cobalt, preferably ruthenium, as active component and rhenium as dopant on a support material, where the total loading of the support material with the active component is from 0.1 to 20% by weight, preferably from 0.2 to 10% by weight, particularly preferably from 0.3 to 5% by weight, and with rhenium is from 0.01 to 20% by weight, preferably from 0.07 to 5% by weight, particularly preferably from 0.08 to 4% by weight, in each case based on the total weight of the catalytically active composition, and the support material preferably comprises a component selected from the group consisting of zeolite A, β-zeolite, mordenite, faujasite, ZSM-5 and MOF.

In a further particularly preferred embodiment of the use according to the invention of the catalytically active composition for the selected methanation of carbon monoxide in reformate streams comprising hydrogen and carbon dioxide, use is made of a catalytically active composition which comprises at least one element selected from the group consisting of ruthenium, rhodium, nickel and cobalt, preferably ruthenium, as active component and rhenium as dopant on a support material, where the total loading of the support material with the active component is from 0.1 to 20% by weight, preferably from 0.2 to 10% by weight, particularly preferably from 0.3 to 5% by weight, and with rhenium is from 0.01 to 20% by weight, preferably from 0.07 to 5% by weight, particularly preferably from 0.08 to 4% by weight, in each case based on the total weight of the catalytically active composition, and the support material preferably comprises a lanthanum-cerium-zirconium oxide, where the support material has a lanthanum oxide content of from 0.1 to 15% by weight, a cerium oxide content of from 0.1 to 20% by weight and a zirconium oxide content of from 30 to 99.8% by weight, based on the weight of the total support material.

The invention likewise provides a process for the selective methanation of carbon monoxide in reformate streams comprising hydrogen and carbon dioxide, wherein a catalytically active composition which comprises at least one element selected from the group consisting of ruthenium, rhodium, nickel and cobalt, preferably ruthenium, as active component and rhenium as dopant on a support material selected from the group consisting of $Al_2O_3$, $ZrO_2$, $TiO_2$, SiC, ZnO, oxides of the Group IIA metals, oxides of the transition metals of Groups IIIB, IVB, VB, VIB, oxides of metals of the rare earths, aluminosilicates, zeolites, MOFs (metal organic frameworks) and mixtures thereof is used.

In a preferred embodiment of the process of the invention for the selective methanation of carbon monoxide in reformate streams comprising hydrogen and carbon dioxide, use is made of a catalytically active composition which comprises at least one element selected from the group consisting of ruthenium, rhodium, nickel and cobalt, preferably ruthenium, as active component and rhenium as dopant on a support material, where the total loading of the support material with the active component is from 0.1 to 20% by weight and with rhenium is from 0.01 to 20% by weight, in each case based on the total weight of the catalytically active composition, and the support material comprises one or more components selected from the group consisting of $Al_2O_3$, $ZrO_2$, $TiO_2$, SiC, ZnO, oxides of the Group IIA metals, oxides of the transition metals of Groups IIIB, IVB, VB, VIB, oxides of metals of the rare earths, aluminosilicates, zeolites, MOFs (metal organic frameworks) and mixtures thereof.

In a particularly preferred embodiment of the process of the invention for the selective methanation of carbon monoxide in reformate streams comprising hydrogen and carbon dioxide, use is made of a catalytically active composition which comprises at least one element selected from the group consisting of ruthenium, rhodium, nickel and cobalt, preferably ruthenium, as active component and rhenium as dopant on a support material, where the total loading of the support material with the active component is from 0.1 to 20% by weight, preferably from 0.2 to 10% by weight, particularly preferably from 0.3 to 5% by weight, and with rhenium is from 0.01 to 20% by weight, preferably from 0.07 to 5% by weight, particularly preferably from 0.08 to 4% by weight, in each case based on the total weight of the catalytically active composition, and the support material preferably comprises a component selected from the group consisting of zeolite A, β-zeolite, mordenite, faujasite, ZSM-5 and MOF.

In a further particularly preferred embodiment of the process of the invention for the selective methanation of carbon monoxide in reformate streams comprising hydrogen and carbon dioxide, use is made of a catalytically active composition which comprises at least one element selected from the group consisting of ruthenium, rhodium, nickel and cobalt, preferably ruthenium, as active component and rhenium as dopant on a support material, where the total loading of the support material with the active component is from 0.1 to 20% by weight, preferably from 0.2 to 10% by weight, particularly preferably from 0.3 to 5% by weight, and with rhenium is from 0.01 to 20% by weight, preferably from 0.07 to 5% by weight, particularly preferably from 0.08 to 4% by weight, in each case based on the total weight of the catalytically active composition, and the support material preferably comprises a lanthanum-cerium-zirconium oxide, where the support material has a lanthanum oxide content of from 0.1 to 15% by weight, a cerium oxide content of from 0.1 to 20% by weight and a zirconium oxide content of from 30 to 99.8% by weight, based on the weight of the total support material.

The selective methanation process of the invention can be performed in a temperature range of preferably from 100 to 300° C.

The selective methanation of CO in a temperature range from 180 to 260° C. is particularly advantageous. This temperature allows direct thermal integration into the preceding low-temperature conversion. This makes it possible to couple the methanation stage according to the invention directly with the low-temperature conversion stage. The high activity combined with high CO selectivity in this temperature range ensures that stable and first and foremost thermally integrated operation of the catalyst is made possible.

The process of the invention is carried out in a mode of operation whose GHSV is in the range from 200 to 20 000 $h^{-1}$, preferably in the range from 500 to 15 000 $h^{-1}$, particularly preferably in the range from 1000 to 10 000 $h^{-1}$ and very particularly preferably in the range from 2000 to 7500 $h^{-1}$. The GHSV "Gas hourly space velocity" is a measure of the gas flow of a reaction gas in liters per liter of catalyst and per hour at standard temperature and standard pressure.

The process of the invention for the selective methanation of carbon monoxide in streams comprising hydrogen and carbon dioxide over the highly active methanation catalyst according to the invention is carried out in conventional apparatuses under customary conditions for carrying out a methanation reaction, as are described, for example, in the Handbook of heterogeneous catalysis, 2nd edition, vol. 1, VCH Verlagsgesellschaft Weinheim, 2008, page 353, and with a process gas comprising CO and hydrogen and being passed over the catalyst.

The process gas suitable for the methanation process is a synthesis gas which can be produced by reforming of solid, liquid and gaseous fuels. As preferred fuels, mention may be made of natural gas, liquefied petroleum gas (LPG), long-chain hydrocarbons (gasoline, diesel) and alcohols such as methanol or ethanol. For the purposes of the present invention, reforming processes are the processes known to those skilled in the art, e.g. steam reforming, partial oxidation and autothermal reforming. Preferred reforming processes are steam reforming and autothermal reforming of hydrocarbons such as natural gas, gasoline and diesel.

The catalytically active composition is thus highly suitable for CO fine purifications in reformate streams comprising hydrogen and carbon dioxide, in particular for use in the production of hydrogen for fuel cell applications.

The invention will be illustrated with the aid of the following examples, without implying a corresponding restriction.

EXAMPLES

Example 1

148.1 g of a lanthanum-cerium-zirconium oxide support (comprising 65% by weight of $ZrO_2$, 15% by weight of $CeO_2$, 5% by weight of $La_2O_3$ and 15% by weight of $Al_2O_3$) were impregnated with an about 30% strength by weight $RuCl_3$ solution, the amount of which was set so that the finished catalyst bore 2% by weight of Ru as active composition. The impregnated support was subsequently dried in a rotary tube furnace at 120° C. for 16 hours and then calcined at 475° C. for 2 hours (at a heating rate of 4° C./min). The ruthenium catalyst obtained in this way was subsequently impregnated with a perrhenic acid solution ($HReO_4$) and dried again at 120° C. for 16 hours. The concentration of perrhenic acid was set so that the finished catalyst after drying comprised 2% by weight of Re as dopant. The BET surface area of the finished catalyst was 83 $m^2/g$*).

Example 2

148.1 g of a lanthanum-cerium-zirconium oxide support (comprising 65% by weight of $ZrO_2$, 15% by weight of $CeO_2$, 5% by weight of $La_2O_3$ and 15% by weight of $Al_2O_3$) were impregnated with an about 30% strength by weight $RuCl_3$ solution, the amount of which was set so that the finished catalyst bore 1% by weight of Ru as active composition. The impregnated support was subsequently dried in a rotary tube furnace at 120° C. for 16 hours and then calcined at 475° C. for 2 hours (at a heating rate of 4° C./min). The ruthenium catalyst obtained in this way was subsequently impregnated with a perrhenic acid solution (HReO$_4$) and dried again at 120° C. for 16 hours. The concentration of perrhenic acid was set so that the finished catalyst after drying comprised 1% by weight of Re as dopant. The BET surface area of the finished catalyst was 86 m$^2$/g*).

The XRD pattern of this catalyst is shown in the figure.

Example 3

148.1 g of a lanthanum-cerium-zirconium oxide support (comprising 65% by weight of ZrO$_2$, 15% by weight of CeO$_2$, 5% by weight of La$_2$O$_3$ and 15% by weight of Al$_2$O$_3$) were impregnated with an about 30% strength by weight RuCl$_3$ solution, the amount of which was set so that the finished catalyst bore 2% by weight of Ru as active composition. The impregnated support was subsequently dried in a rotary tube furnace at 120° C. for 16 hours and then calcined at 475° C. for 2 hours (at a heating rate of 4° C./min). The ruthenium catalyst obtained in this way was subsequently impregnated with a perrhenic acid solution (HReO$_4$) and dried again at 120° C. for 16 hours. The concentration of perrhenic acid was set so that the finished catalyst after drying comprised 0.5% by weight of Re as dopant. The BET surface area of the finished catalyst was 85 m$^2$/g*).

Example 4

148.1 g of a lanthanum-cerium-zirconium oxide support (comprising 65% by weight of ZrO$_2$, 15% by weight of CeO$_2$, 5% by weight of La$_2$O$_3$ and 15% by weight of Al$_2$O$_3$) were impregnated with an about 30% strength by weight RuCl$_3$ solution, the amount of which was set so that the finished catalyst bore 2% by weight of Ru as active composition. The impregnated support was subsequently dried in a rotary tube furnace at 120° C. for 16 hours and then calcined at 475° C. for 2 hours (at a heating rate of 4° C./min). The ruthenium catalyst obtained in this way was subsequently impregnated with a perrhenic acid solution (HReO$_4$) and dried again at 120° C. for 16 hours. The concentration of perrhenic acid was set so that the finished catalyst after drying comprised 0.25% by weight of Re as dopant. The BET surface area of the finished catalyst was 88 m$^2$/g*).

Example 5

148.1 g of a lanthanum-cerium-zirconium oxide support (comprising 65% by weight of ZrO$_2$, 15% by weight of CeO$_2$, 5% by weight of La$_2$O$_3$ and 15% by weight of Al$_2$O$_3$) were impregnated with an about 30% strength by weight RuCl$_3$ solution, the amount of which was set so that the finished catalyst bore 2% by weight of Ru as active composition. The impregnated support was subsequently dried in a rotary tube furnace at 120° C. for 16 hours and then calcined at 475° C. for 2 hours (at a heating rate of 4° C./min). The ruthenium catalyst obtained in this way was subsequently impregnated with a perrhenic acid solution (HReO$_4$) and dried again at 120° C. for 16 hours. The concentration of perrhenic acid was set so that the finished catalyst after drying comprised 0.1% by weight of Re as dopant. The BET surface area of the finished catalyst was 86 m$^2$/g*).

The BET surface area of the respective catalysts according to the invention was determined in accordance with DIN 66131.

Example 6 (Comparative Example)

Reproduction of the Patent EP 2 125 201 B1, Example 7d

A support composed of 70% by weight of ZrO$_2$, 15% by weight of CeO$_2$, 5% by weight of La$_2$O$_3$ and 10% by weight of Al$_2$O$_3$ was admixed with an RuCl$_3$ solution, the concentration of which was set so that the calcined end product bore 2% by weight of Ru as active composition.

Example 7 (Comparative Example)

147 g of a γ-Al$_2$O$_3$ support (0.8 mm spheres, Sasol GmbH) were impregnated with an about 30% strength by weight RuCl$_3$ solution, the amount of which was set so that the finished catalyst bore 2% by weight of Ru as active composition. The impregnated support was subsequently dried in a rotary tube furnace at 120° C. for 16 hours and then calcined at 475° C. for 2 hours (at a heating rate of 4° C./min).

TABLE 1

Composition of the catalysts of examples 1 to 7

| Catalyst | Ru [% by weight] | Re [% by weight] | Support |
| --- | --- | --- | --- |
| Example 1 | 2 | 2 | LaCeZr oxide |
| Example 2 | 2 | 1 | LaCeZr oxide |
| Example 3 | 2 | 0.5 | LaCeZr oxide |
| Example 4 | 2 | 0.25 | LaCeZr oxide |
| Example 5 | 2 | 0.10 | LaCeZr oxide |
| Example 6* | 2 | 0 | LaCeZr oxide |
| Example 7* | 2 | 0 | Al$_2$O$_3$ |

*Comparative examples

Example 8—Selective Methanation Using the Catalysts from Examples 1 to 7

Test Conditions:

An electrically heated fixed-bed tube reactor having a length of 530 mm and an internal diameter of 10 mm was used for the experiment.

5 ml of steatite spheres having a diameter of from 1.8 to 2.2 mm were firstly installed, and the catalyst mixture was subsequently placed on these. The catalyst mixture consisted of about 20 ml of catalyst pellets (1.5×1.5 mm). 5 ml of steatite spheres having a diameter of from 1.8 to 2.2 mm, which filled the remaining volume of the reactor, served as guard bed.

The catalyst was firstly reduced using 90 l/h of nitrogen and 10 l/h of hydrogen at 230° C. for one hour. The gas composition selected for the experiment is typical of the output of the low-temperature shift stage after the reforming of methane and was 22% by volume of H$_2$, 28% by volume of N$_2$, 25% by volume of H$_2$O, 13% by volume of CO$_2$, 5% of volume of CO and 0.5% by volume of CH$_4$. All experiments were carried out at a pressure of 2 bara and a space velocity of 5000 l·h$^{-1}$·l$^{-1}_{cat}$.

After all gases had been set and the reactor had (after the reduction at 230° C.) been heated to a temperature of 260° C., the experiment was started and the selectivity of the catalysts used in each case was monitored over a period of 90 hours.

The concentration of the gases was determined by means of on-line GC downstream of the reactor.

The parameters selectivity at conversion were employed for evaluating the results of the experiments. The selectivity is the ratio of the amount of CO reacted and the amount of methane formed (in % by volume). The conversion is based on CO.

Results:

The catalysts were measured under the abovementioned conditions. Complete conversion of CO (CO content=0 ppm, or below the detection limit of the GC instrument) could be achieved under these experimental conditions for all catalysts from examples 1 to 7.

The CO selectivities at the beginning of the respective experiment [start of run (SOR)] and after a time on stream (TOS) of 90 hours are reported in table 2.

As can be seen from table 2, the CO selectivity dropped significantly to values of 18 and 24% after a time of operation of 90 hours when using the comparative catalysts from examples 6 and 7, while in the case of the inventive catalysts from examples 1 to 5 a CO selectivity in the range from 46% to 53% was still observed.

TABLE 2

Results of the selective methanation of CO

| Catalyst | Active composition/doping element Support | Selectivity at 260° C. Start of Run | After 90 hours TOS |
|---|---|---|---|
| Example 1: | 2% by weight of Ru/2% by weight of Re LaCeZr oxide | 83% | 51% |
| Example 2: | 2% by weight of Ru/1% by weight of Re LaCeZr oxide | 84% | 53% |
| Example 3: | 2% by weight of Ru/0.5% by weight of Re LaCeZr oxide | 82% | 49% |
| Example 4: | 2% by weight of Ru/0.25% by weight of Re LaCeZr oxide | 80% | 45% |
| Example 5: | 2% by weight of Ru/0.1% by weight of Re LaCeZr oxide | 82% | 46% |
| Example 6: | 2% of Ru/ LaCeZr oxide | 81% | 24% |
| Example 7: | 2% of Ru/ $\gamma$-$Al_2O_3$ | 80% | 18% |

TABLE 3

Selectivity profile after a time of operation of 90 hours at 260° C. and subsequent stepwise lowering of the temperature by in each case 20° C. over a period of 4 hours. The selectivity values indicated were determined at complete conversion of CO (0 ppm of CO). In the case of an incomplete conversion, the selectivity was reported as: =not applicable (n/a). (Test conditions: T = 200-260° C., p = 2 bar, GHSV = 5000 h$^{-1}$, inlet gas composition: 5% of CO, 13% of $CO_2$, 0.5% of $CH_4$, 22% of $H_2$, 25% of $H_2O$, 28% of $N_2$)

| Catalyst | Active composition/doping element Support | Selectivity profile after 90 h at various temperatures | | | |
|---|---|---|---|---|---|
| | | 260° C. | 240° C. | 220° C. | 200° C. |
| Example 1 | 2% by weight of Ru/2% by weight of Re LaCeZr oxide | 49% | 67% | 87% | n/a |
| Example 2 | 2% by weight of Ru/1% by weight of Re LaCeZr oxide | 50% | 62% | 81% | 100% |
| Example 3 | 2% by weight of Ru/0.5% by weight of Re LaCeZr oxide | 49% | 66% | 83% | 97% |
| Example 4 | 2% by weight of Ru/0.25% by weight of Re LaCeZr oxide | 45% | 61% | 79% | 95% |
| Example 5 | 2% by weight of Ru/0.1% by weight of Re LaCeZr oxide | 46% | 58% | 77% | 95% |
| Example 6 | 2% of Ru LaCeZr oxide | 24% | 36% | 57% | 88% |
| Example 7 | 2% of Ru $\gamma$-$Al_2O_3$ | 18% | 32% | 54% | 95% |

As can be seen from table 3, the rhenium-doped ruthenium catalysts according to the invention from examples 1 to 5 display significantly higher CO selectivities over the temperature range from 200 to 260° C. than the two rhenium-free catalysts from comparative examples 6 and 7.

The invention claimed is:

1. A catalytically active composition for the selective methanation of carbon monoxide in reformate streams comprising hydrogen and carbon dioxide, comprising at least one element selected from the group consisting of ruthenium, rhodium, nickel and cobalt as active component and rhenium as dopant on a lanthanum-cerium-zirconium oxide support material;
   wherein the active component is present in an amount of from 0.1 to 20% by weight and rhenium is present in an amount of from 0.01 to 20% by weight, in each case based on the total amount of the catalytically active composition;
   wherein the support material is in the form of a shaped body with a compressive strength of at least 0.2 kgf;
   wherein the support material has a pore volume of from 0.05 to 1.5 $cm^3/g$.

2. The catalytically active composition according to claim 1, wherein the composition comprises ruthenium as active component.

3. The catalytically active composition according to claim 1, wherein the support material comprises lanthanum oxide in an amount of from 0.1 to 15% by weight, cerium oxide in an amount of from 0.1 to 20% by weight and zirconium oxide in an amount of from 30 to 99.8% by weight, in each case based on the total amount of the support material.

4. The catalytically active composition according to claim 1, wherein the rhenium is present in an amount of from 0.1 to 2% by weight, based on the total amount of the catalytically active composition.

5. The catalytically active composition according to claim 4, wherein the active component is present in an amount of 2% by weight, based on the total amount of the catalytically active composition.

6. The catalytically active composition according to claim 1, wherein the active component is Ru.

7. The catalytically active composition according to claim 1, wherein the catalytically active composition has a BET surface area of at least 20 $m^2/g$.

8. The catalytically active composition according to claim 6, wherein the catalytically active composition comprises 0.07 to 5% by weight of rhenium and 0.7 to 4% by weight of ruthenium, based on the total weight of the catalytically active composition.

9. The catalytically active composition according to claim 6, wherein the catalytically active composition comprises 0.08-4% by weight of rhenium and from 1 to 3% by weight of ruthenium, based on the total weight of the catalytically active composition.

10. The catalytically active composition according to claim 6, wherein the catalytically active composition comprises 2% by weight of ruthenium and 0.1-2% by weight of rhenium, based on the total weight of the catalytically active composition.

11. A process for producing a catalytically active composition according to claim 1, which comprises the steps of bringing the active component and the dopant into solution and applying the solution to the support material by impregnation.

12. The process for producing a catalytically active composition according to claim 1, which comprises the steps of kneading the support material with the salts and/or hydrates of the active component and of the dopant and subsequently extruding and drying the mixture.

13. A process comprising selectively methanating carbon monoxide in the presence of catalytically active composition according to claim 1.

14. The process according to claim 13, wherein the methanation is carried out in a temperature range from 100 to 300° C.

15. The process according to claim 13, wherein it directly follows a low-temperature conversion stage.

* * * * *